United States Patent [19]

Jon et al.

[11] 4,417,478

[45] Nov. 29, 1983

[54] METHOD FOR DETERMINING LEAD FRAME FAILURE MODES USING ACOUSTIC EMISSION AND DISCRIMINANT ANALYSIS TECHNIQUES

[75] Inventors: Min-Chung Jon, East Windsor Township, Mercer County; Vito Palazzo, Hamilton Township, Mercer County; George W. Sturm, Ewing Township, Mercer County, all of N.J.

[73] Assignee: Western Electric Co., Inc., New York, N.Y.

[21] Appl. No.: 325,940

[22] Filed: Nov. 30, 1981

[51] Int. Cl.³ ............................................. G01N 29/00
[52] U.S. Cl. ........................................ 73/801; 73/587
[58] Field of Search ............ 73/587, 801, 588, 750 A, 73/827, 658, 659

[56] References Cited

U.S. PATENT DOCUMENTS

| | | | |
|---|---|---|---|
| 4,107,981 | 8/1978 | Kanagawa | 73/587 X |
| 4,207,771 | 6/1980 | Carlos et al. | 73/587 |
| 4,232,558 | 11/1980 | Jon et al. | 73/801 |
| 4,297,885 | 11/1981 | Hein, Jr. et al. | 73/587 |
| 4,317,368 | 3/1982 | McElroy | 73/587 |

OTHER PUBLICATIONS

Monitoring Crack Growth in Ceramic by Acoustic Emission, Materials Evaluation, Dec. 1970, pp. 267–270, by Romrell.
Intro. to Multivariate Statistical Analysis; by Anderson, T. W., John Wiley & Sons Inc., 1958 pp. 5–58.

Primary Examiner—Stephen A. Kreitman
Attorney, Agent, or Firm—M. M. de Picciotto

[57] ABSTRACT

An automatic pull tester and an acoustic emission system are herein combined to analyze the failure modes of lead frames bonded to integrated circuits. By using a discriminant analysis technique, a specific failure mode can be determined in real-time by first measuring up to five variables during the pulling operation. The five variables that may be measured comprise acoustic emission signals of a first amplitude (AE1), acoustic emission signals of a second amplitude (AE2), the time elapsed until failure ($\Delta t$), the number (n) of acoustic emission bursts above a first threshold, to the peak pulling force at failure ($L_{max}$). Next, the variables measured are incorporated into a plurality of predetermined functions, each function corresponding to one failure mode (FM1 to FM5). The failure mode of the bond is determined by selecting the function having the highest value (FIG. 4).

10 Claims, 11 Drawing Figures

METHOD FOR DETERMINING LEAD FRAME FAILURE MODES USING ACOUSTIC EMISSION AND DISCRIMINANT ANALYSIS TECHNIQUES

TECHNICAL FIELD

The present invention relates to a real-time evaluation of failure modes of bonded articles, and more particularly to a method for determining lead frame failure modes during destructive testing.

BACKGROUND OF THE INVENTION

Thermocompression (TC) bonding is often used in the manufacturing of electronic components for joining external leads to integrated circuit substrates. TC bonds between two articles are generally reliable when optimum parameters of time, temperature and pressure between the two articles are used. Several attempts for determining lead frame bond failure modes of film integrated circuits from automatic pull testers use only visual examinations of the lead frame bond area. Such time consuming processes of visual inspection by means of low power optical microscopes cannot fully characterize the failure modes because conventional visual inspection cannot reveal a fine microstructure, and the observation of the surface shows only the debris remaining after the dynamic process has ceased. Thus, for two failure modes possessing a similar morphology, conventional visual inspection cannot differentiate one from the other. Furthermore, there can be wide variations in failure mode classification between different operators observing the same bonds, and misclassifications can occur when large numbers of bonds are being inspected and operator fatigue becomes a factor.

A known method combining acoustic emission (AE) data with automatic pull testers to determine failure modes of bonded articles is described in U.S. Pat. No. 4,232,558 issued on Nov. 11, 1980 to M. C. Jon and V. Palazzo and assigned to the assignee herein. Such a known method comprises the steps of monitoring the AE signals emanating from the bonded articles during a destructive test, developing a signal proportional to the manner of excursions of the AE signals above a predetermined threshold, and comparing the developed signal to empirically determined ranges of signals to determine the bond failure mode. Such a known method clearly overcomes the above-mentioned limitations and disadvantages of visual inspection. Although the just-described prior art technique operates satisfactorily for its intended purpose, i.e., as a method for determining bond failure modes wherein the subjective and often inaccurate visual inspection is substantially eliminated this method is based on the comparison of AE counts with empirically determined counts resulting in some scatter and overlap of data. The foregoing may lead to misclassifications of failure modes in regions of substantial overlap of AE counts. In other words, there exists a need for more accurately systematically and consistently determined the failure modes of bonded articles subjected to destructive testing.

SUMMARY OF THE INVENTION

The foregoing problem is solved by an embodiment of the present invention wherein a destructive testing method for determining the failure mode of articles, bonded together, comprises the step of applying a destructive pulling force to one of the bonded articles, measuring at least one variable associated with the destructive test, the variable being selected from a group comprising: (a) first acoustic emission signals emanating from the bonded articles during the destructive test and having amplitudes above a first threshold, (b) second acoustic emission signals emanating from the bonded articles during the destructive test and having amplitudes above a second threshold, (c) elapsed time until failure, (d) number of acoustic emission bursts above the first threshold during the destructive test and (e) peak load applied to the bonded articles until failure. The present method further comprises the steps of incorporating the at least one measured variable into a plurality of predetermined discriminant functions, each one of the discriminant functions corresponding to one failure mode of a plurality of failure modes; and selecting out of the plurality of discriminant functions the discriminant function having the highest value thereby determining the corresponding failure mode of the articles.

One advantage of the present invention is to accurately and consistently identify failure modes of articles without visual inspection of the articles after destruction.

Another advantage of the present invention is to achieve a real-time failure mode determination by means of discriminant analysis functions that can be incorporated into a microprocessing unit.

A further advantage of the present invention is to enable a multi-dimensional failure mode analysis, i.e., a determination of the failure mode based on several variables associated with the destructive test.

A still further advantage of the present invention is its capability of investigating problems associated with the quality of the substrate material, the bond, and/or the lead.

DETAILED DESCRIPTION

Figure 1:
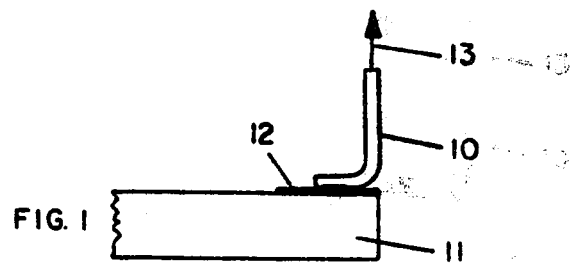
FIG. 1 illustratively shows a bond, e.g., a thermocompression (TC) bond, between a terminal lead and a substrate body.

Schematically shown in FIG. 1 is a bond between a lead 10, e.g., a gold plated lead, and a substrate 11, e.g., a ceramic substrate, with a thin gold coating 12 positioned therebetween. Although the present invention will hereafter be described in connection with thermocompression bonds between gold plated leads and gold plated regions of a ceramic substrate, it will be readily appreciated that the disclosed method is also applicable to other bonding techniques such as soldering, welding, brazing, etc. It will be further understood that the substrate material may be of any well known type, e.g., aluminum oxide, silicon oxide, beryllium oxide, without departing from the spirit and scope of the present invention.

In order to determine during the production of a certain type of film integrated circuit whether the bond between lead 10 and substrate 11 is acceptable a sample number of bonded leads are pulled to destruction by applying a pulling force thereto as illustratively shown by arrow 13. Such a sample number may be, for example, one circuit out of every two hundred circuits produced. The determination of the type of failure mode of the bond under test will enable an adjustment of the various bonding parameters thereby yielding better, stronger and more reliable bonds.

Figure 2A:
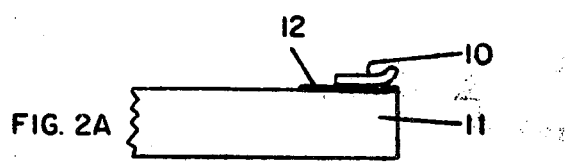
FIGS. 2A to 2E show five possible failure modes of the TC bond of FIG. 1.

Illustratively shown in FIGS. 2A to 2E are five possible failure modes of the bond between lead 10 and substrate 11 resulting from the application of the pulling force 13. FIG. 2A shows one failure mode wherein a portion of lead 10 breaks away as the result of pulling force 13. Such a mode is called "lead failure" and will be identified herein as FM1.

Figure 2B:
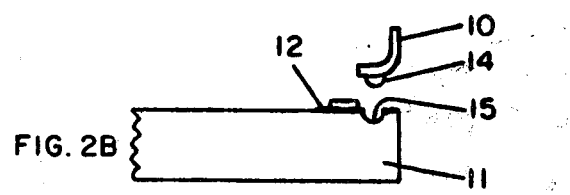
Figure 2C:
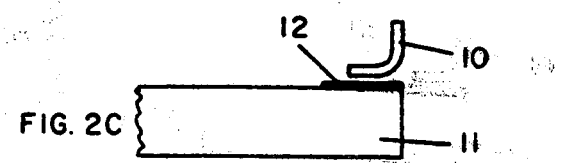
Figure 2D:
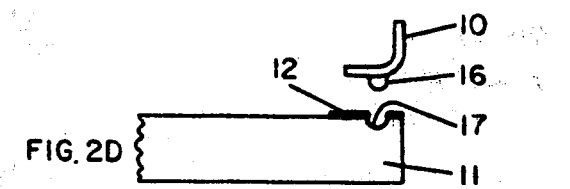
Figure 2E:
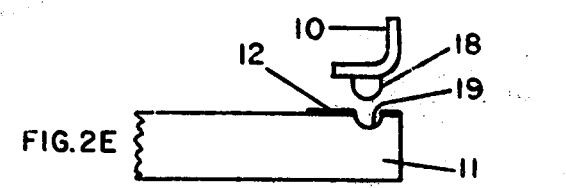

Referring now to FIG. 2B, a second failure mode is shown wherein lead 10 fails and a small ceramic portion 14 is pulled out of substrate 11 leaving a small notch 15 therein. Such a mode called "lead failure with some ceramic pullout" will be identified hereafter as FM2. FIG. 2C illustratively shows a bond failure, i.e., a "gold-to-gold" failure which will be identified hereafter as FM3. A "gold-to-gold failure with some ceramic pull-out" is shown in FIG. 2D wherein a small ceramic portion 16 is pulled out of substrate 11 leaving a small cavity or notch 17 therein. Such a failure mode is referenced herein as FM4. In FIG. 2E, a failure mode identified hereafter as FM5 is shown which corresponds to a "ceramic pullout." The latter is distinguishable by a major portion of ceramic material 18 being pulled out of the substrate 11 as the result of the pulling force 13 thereby leaving a cavity 19 in the substrate.

Figure 3:
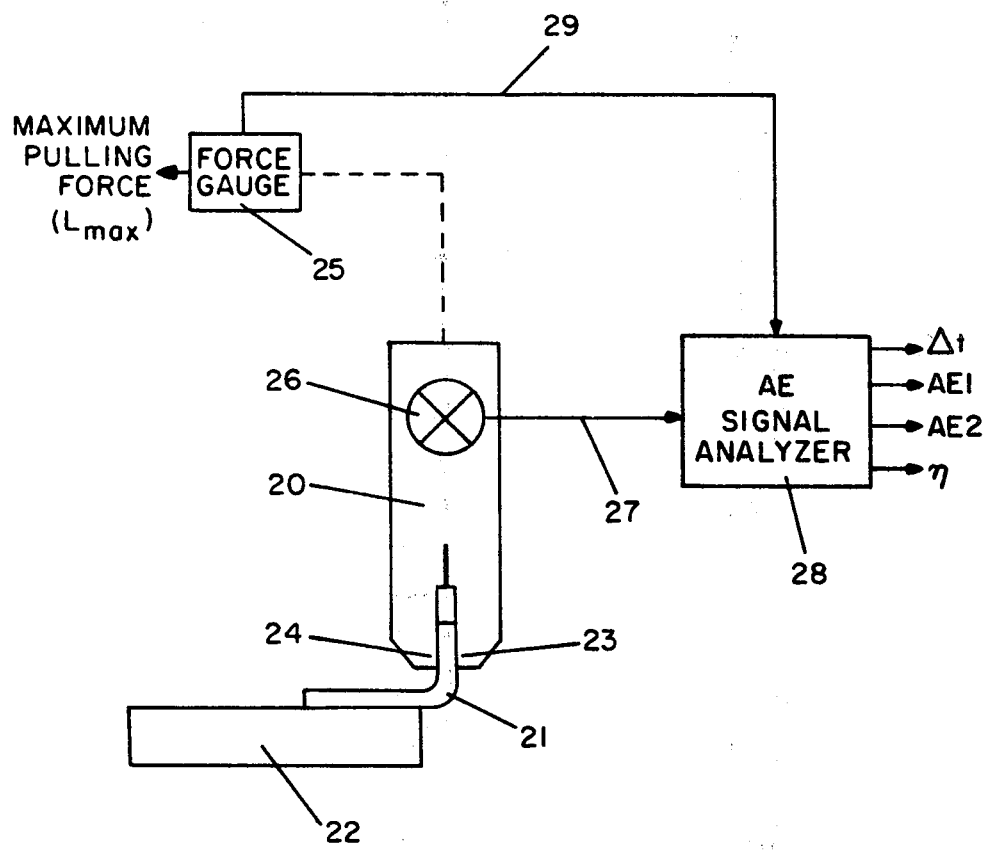
FIG. 3 schematically shows a destructive pull testing equipment.

Schematically shown in FIG. 3 is a destructive pull testing equipment which comprises two main parts. First, an automatic pull tester having a grasping mechanism 20 for firmly holding a lead under test 21 between a pair of clamping jaws 23 and 24. A force gauge 25 is coupled to the grasping mechanism 20 and is adapted to record the maximum load or pulling force applied to the lead under test 21. The second part of the destructive testing equipment comprises an acoustic emission monitoring system which includes a transducer 26 fixedly mounted on the grasping mechanism 20 and capable of detecting acoustic emission signals generated in response to the pulling force applied to the lead 21. The output signals generated by transducer 26 and available on lead 27 are processed in an acoustic emission (AE) signal analyzer 28. The AE signal analyzer is coupled to the force gauge 25 via a lead 29.

In analyzing the failure mode of a TC bonded lead frame during the destructive pull testing, five variables are measured: they are the peak pulling force ($L_{max}$) the lead fails at; the time ($\Delta t$) it takes to fail; the number (n) of AE bursts or events; the number (AE1) of AE crossings above a low level threshold; and the number (AE2) of AE crossings above a high level threshold. Four of these variables, namely, the low threshold AE1 count, the high threshold AE2 count, $\Delta t$, and the event count n are processed by the analyzer 28 of FIG. 3. The fifth variable, i.e., the peak force at failure, $L_{max}$, is generated by the force gauge 25 of the automatic pull tester and is available for further processing.

Figure 4:
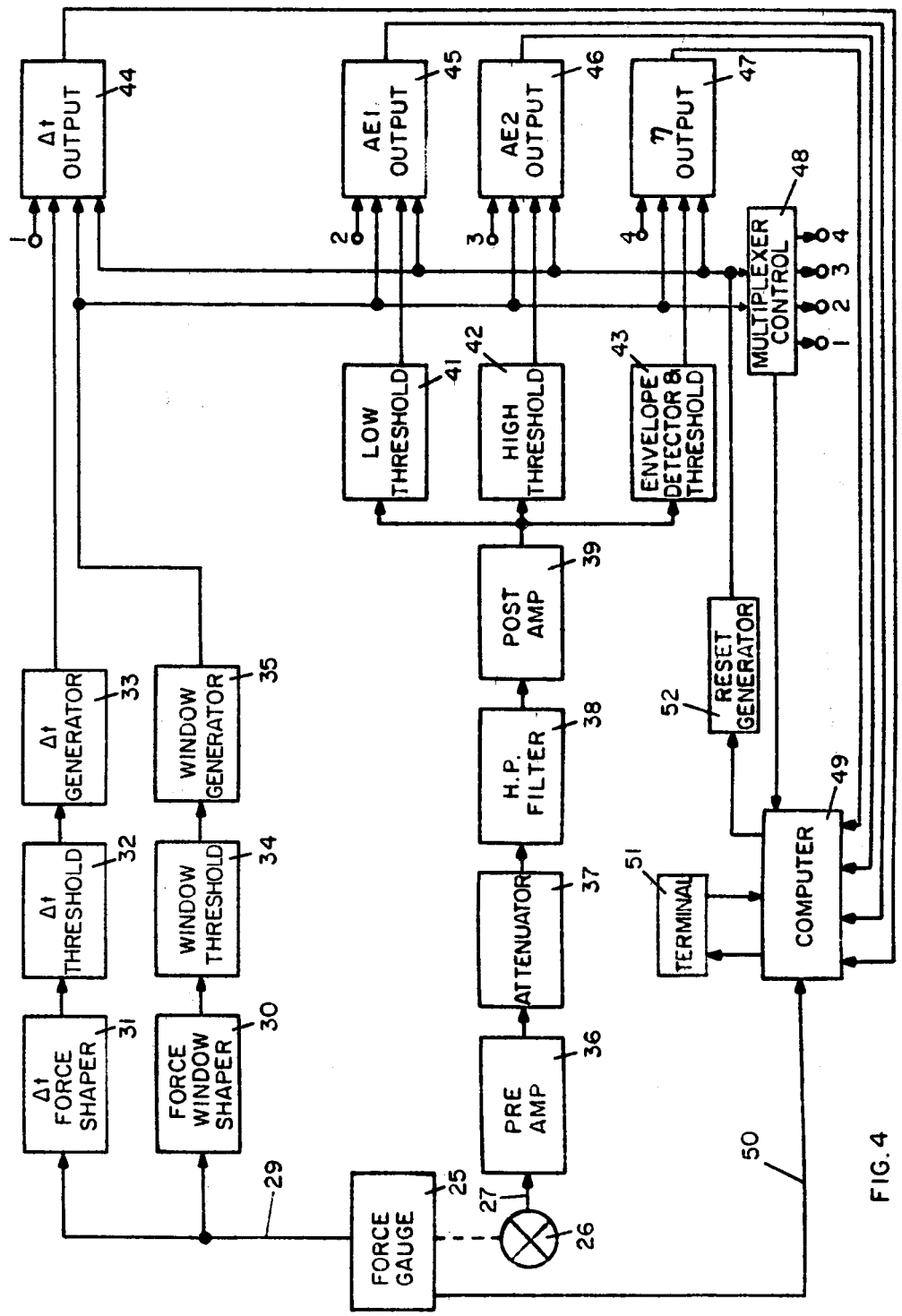
FIG. 4 shows a block diagram circuit of the acoustic emission testing system.

Referring now to FIG. 4, the force gauge 25 generates a signal on output lead 29 which is proportional to the force applied on the lead frame (not shown) which is being pulled. This signal is amplified, filtered and shaped by the analog force window shaper 30 and the analog force $\Delta t$ shaper 31. The output from the $\Delta t$ shaper circuit is coupled to the $\Delta t$ threshold detector circuit 32, the output of which is a pulse having a length equal to the time during which the force on the lead being pulled is above a given nominal force value. This pulse is used to gate a pulse generator 33 and the gated pulses are then counted thus giving the time it takes the lead to fail. The output of the analog force window 30 is coupled to a threshold circuit 34 and a window generator 35 whose output is a pulse which begins before the $\Delta t$ pulse starts and ends after the $\Delta t$ pulse. Only information generated during this window time interval is analyzed.

The AE transducer 26 placed on the jaw assembly of the automatic pull tester as illustratively shown in FIG. 3, generates a low level signal. The latter is coupled to a low noise preamplifier 36 the output of which is coupled to an attenuator 37, a high pass filter 38, and a post-amplifier 39. The output signals of post-amplifier 39 are generally of the type shown in the above-referenced U.S. Pat. No. 4,232,558, which is herein incorporated by reference. Two threshold detector circuits, a low threshold detector 41 and a high threshold detector 42, are coupled to post-amplifier 39 for generating pulses for each excursion of the amplified signals respectively above a low threshold and a high threshold. An envelope detector and threshold circuit 43 is coupled to post-amplifier 39 for generating the number of envelopes or bursts, n, which is indicative of the number of discrete AE events generated during a destructive test. The envelope signal follows the voltage peaks of the amplified AE signal.

Each of the four variables analyzed, i.e., $\Delta t$, AE1, AE2, and n, is coupled to a corresponding output circuit 44, 45, 46 and 47 which, under the control of the window generator 35 and a multiplexer control circuit 48, gathers the data and delivers it to a computer 49 for further processing. Each one of the output circuits 44 to 47 is gated by the window signal generated by window generator 35 such that the various variables $\Delta t$, AE1, AE2 and n are delivered to the computer 49 after the end of the window time interval. The fifth variable, i.e., the peak load at failure, $L_{max}$, is delivered to the computer 49 by the force gauge 25 via coupling lead 50. After the computer 49 has collected and has processed all of the data, and the failure mode of the lead under test is identified and outputted on terminal 51, a reset signal is generated by reset generator 52 indicating that a next pull test may be initiated. This reset signal is used to reset all of the variable output circuits 44 to 47 as well as the multiplexer circuit 48 thereby preparing the analyzer for the next pull test.

Figure 5:
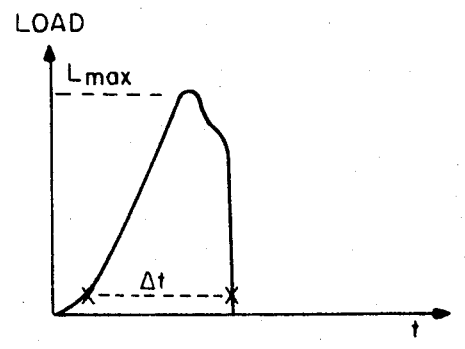
FIGS. 5a to 5c shows the various acoustic emission signals generated by the equipment of FIG. 4.
Figure 5:
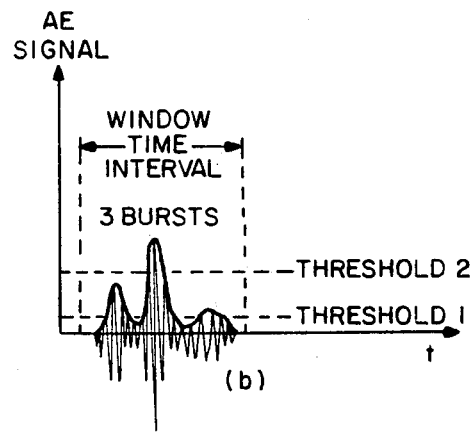
Figure 5:
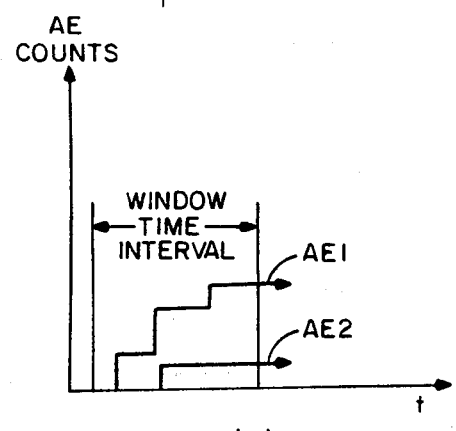

FIG. 5 shows schematically the variables generated by the AE signal analyzer of FIG. 4. The analyzer provides measurements of the time to failure ($\Delta t$) of the bond, the number of AE bursts during the window time interval, i.e., during the destructive test, and the number of AE threshold crossing counts during the window time interval. The AE analyzer 28 in FIG. 3 receives the gating signal generated by the force gauge 25 to initiate the AE information processing. As long as the gauge gating voltage exceeds a predetermined level, AE information is collected and processed during the window time interval. Shown in FIG. 5a is the peak load, $L_{max}$, applied to the lead. AE threshold crossing counts AE1 and AE2 shown in FIG. 5c are generated by the AE signals, respectively, having a voltage amplitude in excess of the first and the second predetermined dc threshold voltage and occuring during the window time interval. The other AE output data signal, generated and/or displayed by the AE signal analyzer 28 is shown in FIG. 5b and corresponds to the number of bursts, n, of the AE signals occuring during the window time interval. The number of bursts, n, is determined by analyzing the envelope signal of the AE signals during the window time interval. The number of bursts, n, is indicative of the number of discrete AE events generated during a destructive test.

As described above, during each destructive pull testing, the automatic pull tester and the AE monitoring system may measure up to five variables AE1, AE2, Δt, n, and $L_{max}$ for each lead that has been pulled to failure. As explained in connection with FIGS. 2A to 2E, there are five identifiable failure modes FM1–FM5. The present invention is specifically directed to a method for determining failure modes of the lead frame bond that has been pulled to failure out of one of the above five failure modes FM1 to FM5 on the basis of at least one variable out of the five variables measured.

In accordance with an illustrative embodiment of the present invention, a discriminant analysis technique is used to achieve the foregoing determination. The applicability of discriminant analysis to failure mode determination enables the classification of several failure modes on the basis of a number of variables measured. More specifically, let $\vec{Z}$ be a p-dimensional random vector whose elements are the p measured variables. In other words, with reference to the acoustic emission testing system of FIG. 4, let:

$$\vec{Z} = (AE1, AE2, \Delta t, n, L_{max}) \quad (1)$$

Applicants' invention is then directed to determine in which one of the five failure modes FM1–FM5 the multidimensional vector $\vec{Z}$ belongs.

Each one of the five failure modes FM1 to FM5 is assumed to follow a multivariate normal distribution of dimension p with parameters $\vec{a}_i$ and $\vec{b}_i$ (wherein p is the number of variables measured, and $i=1, \ldots, 5$). The multivariate normal distribution and parameters $\vec{a}_i$ and $\vec{b}_i$ are explained in Chapters 2 and 3 of T. W. Anderson's book entitled "An Introduction to Multivariate Statistical Analysis" published in 1958 by John Wiley & Sons, Inc. Using the matrix notation of T. W. Anderson, the functional form for the density of failure mode i, with $i=1, \ldots, 5$ is $FM_i(\vec{Z}, \vec{a}_i, \vec{b}_i)$ and is given by:

$$[(2\pi)^p |\vec{b}_i|]^{-\frac{1}{2}} \exp[-\frac{1}{2}(\vec{Z}-\vec{a}_i)'\vec{b}_i^{-1}(\vec{Z}-\vec{a}_i)] \quad (2)$$

where
$\vec{Z} = (AE1, AE2, \Delta t, n, L_{max})$ is a vector of real numbers in p=5 dimensional space;
$\vec{a}_i$ = mean vector for failure mode i;
$\vec{b}_i$ = covariance variance matrix for failure mode i; and
$|b_i|$ = determinant of matrix $\vec{b}_i$.
Equation (2) is of the same type as equation (23) given at page 14 of T. W. Anderson's above-referenced book.

Assuming that the $a_i$'s and $b_i$'s ($i=1, \ldots, 5$) are known, then a classification criterion that maximizes the probability of correct classification is that $\vec{Z}$ belongs to failure mode j if:

$$FM_j(\vec{Z}, \vec{a}_j, \vec{b}_j) > FM_i(\vec{Z}, \vec{a}_i, \vec{b}_i) \text{ for all } i \neq j (i=1, \ldots, 5). \quad (3)$$

In other words, the failure mode with the largest density value at the point $\vec{Z}$ is the one from which $\vec{Z}$ most likely came.

Figures 6, 7:
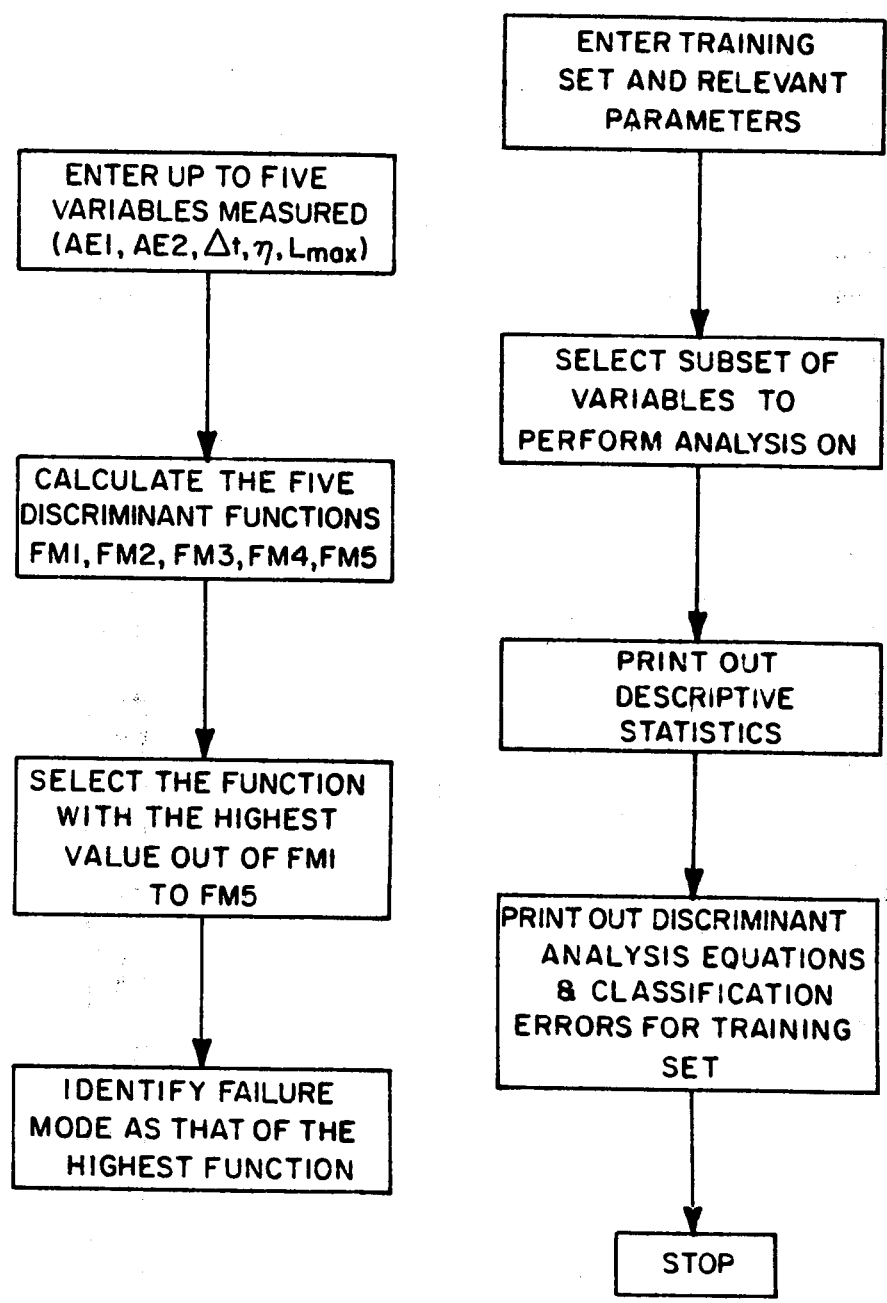
FIG. 6 is a flow chart of the various steps of the present method.
FIG. 7 is a flow chart of a computer program for generating the various discriminant analysis functions.

Shown in FIG. 6 is a flow chart of the above-described method. The latter, which is implemented by the computer 49 of FIG. 4, comprises the steps of first entering any of the five variables measured; then calculating each one of the five discriminant functions FM1, FM2, FM3, FM4 and FM5 given by the above equation (2); then selecting the function with the highest value; and determining the failure mode of the lead under test as that of the highest function.

In the above analysis, the parameters $\vec{a}_i$ and $\vec{b}_i$ ($i=1, \ldots, 5$) are usually not known for each failure mode. Therefore, estimates of these parameters will have to be made. In order to achieve such estimation, a random sample of observations from each failure mode is needed. This random sample of observations is called a training set. If $\vec{Z}_{1i}, \vec{Z}_{2i}, \ldots \vec{Z}_{n_i i}$ is a random sample of size $n_i$ from failure mode i ($i=1, \ldots, 5$) then the sample mean vector $\vec{a}_i$ for failure mode i becomes:

$$\vec{a}_i = \frac{1}{n_i} \sum_{j=1}^{n_i} \vec{Z}_{ji} \quad (4)$$

Parameter $\vec{b}_i$, i.e., the sample covariance variance matrix for failure mode i, is given by:

$$\vec{b}_i = \sum_{j=1}^{n_i} (\vec{Z}_{ji} - \vec{Z}_i)(\vec{Z}_{ji} - \vec{Z}_i)'/(n_i - 1) \quad (5)$$

by substituting the above estimated $\vec{a}_i$ and $\vec{b}_i$ *parameters given by equations* (4) and (5) for $\vec{a}_i$ and $\vec{b}_i$ in equation (2), the classification criterion expressed in equation (3) shows that $\vec{Z}$ belongs to failure mode j if:

$$FM_j(\vec{Z}, \vec{a}_j, \vec{b}_j) > FM_i(\vec{Z}, \vec{a}_i, \vec{b}_i) \text{ for all } i \neq j (i=1, \ldots, 5). \quad (6)$$

An interactive computer program for generating the above discriminant analysis functions was developed, and the flow chart for this program is shown in FIG. 7. First, the data of a training set which includes the visually identified failure mode for each lead is typed into a file which is stored on a computer. The discriminant analysis program is then used to analyze this data so as to calculate the functions $FM_i$ given by equation 2. The variables to be included in the analysis can be chosen in any combination, e.g., using any one of the five variables; or only AE1, Δt, AE2; or using all five variables. After the analysis is performed, the program prints out the following information:
1. mean vectors and variances (i.e., the $\vec{a}_i$ and $\vec{b}_i$);
2. test statistics and fail probability for testing the equality of mean vectors;
3. linear discriminant equations for the five failure modes (i.e., the FM1 to FM5 functions); and
4. the predicted classification and the probability of error for each observation in the training set.

The linear discriminant equations can be used to classify any new set of data as long as the same kind of circuits are tested for failure mode classification.

By storing the five discriminant functions related to the five failure modes in computer 49 of FIG. 4, the failure mode can be determined using these functions and be outputted to terminal 51 at the end of the pull testing. As shown in FIG. 6, this is done by gathering data of number of bursts n; peak load $L_{max}$; AE1; $\Delta t$; and AE2, and by sending these data to the computer 49 where the calculations are performed using the discriminant functions. The failure mode that has the highest probability of correct classification is then outputted to terminal 51 as the failure mode for a tested TC lead. By the end of the pull testing, all the failure modes are determined. This process eliminates the tedious optical visual inspection and provides an accurate and consistent method for determining failure modes.

The foregoing illustrative embodiment has been presented merely to illustrate the pertinent inventive concepts. Numerous modifications can be made by those skilled in the art without departing from the spirit and scope of the invention.

What is claimed is:

1. A destructive testing method for determining the failure mode of articles, bonded together, comprising the steps of:

applying a destructive pulling force to one of the bonded articles;
   measuring at least one variable associated with the destructive test, the variable being selected from a group comprising:
   (a) first acoustic emission signals emanating from the bonded articles during the destructive test and having amplitudes above a first threshold,
   (b) second acoustic emission signals emanating from the bonded articles during the destructive test and having amplitudes above a second threshold,
   (c) elapsed time until failure,
   (d) number of acoustic emission bursts above said first threshold during the destructive test, and
   (e) peak load applied to the bonded articles until failure;
   incorporating said at least one measured variable into a plurality of predetermined discriminant functions, each one of said discriminant functions corresponding to one failure mode of a plurality of failure modes; and
   selecting out of said plurality of discriminant functions the discriminant function having the highest value thereby determining the corresponding failure mode of the articles.

2. A method according to claim 1, comprising measuring two variables out of said group of variables, and incorporating said two measured variables into the plurality of discriminant functions.

3. A method according to claim 1, comprising measuring three variables out of said group of variables, and incorporating said three measured variables into the plurality of discriminant functions.

4. A method according to claim 1, comprising measuring four variables out of said group of variables, and incorporating said four measured variables into the plurality of discriminant functions.

5. A method according to claim 1, comprising measuring all the variables of said group of variables, and incorporating said measured variables into the plurality of discriminant functions.

6. A destructive testing method for determining the failure mode of a lead bonded to a substrate comprising the steps of:

applying a pulling force to the lead;
   measuring at least one variable associated with the destructive test, the variable being selected from a group comprising:
   (a) first acoustic emission signals emanating from the bond between the lead and the substrate during the destructive test and having amplitudes above a first threshold,
   (b) second acoustic emission signals emanating from the bond between the lead and the substrate during the destructive test and having amplitudes above a second threshold,
   (c) elapsed time until failure,
   (d) number of acoustic emission bursts above said first threshold during the destructive test, and
   (e) peak load applied to the lead until failure;
   incorporating said at least one measured variable into a plurality of predetermined discriminant functions, each one of said discriminant functions corresponding to one failure mode of a plurality of failure modes; and
   selecting out of said plurality of discriminant functions the discriminant function having the highest value thereby determining the corresponding failure mode of the bond between the lead and the substrate.

7. A method according to claim 6, comprising measuring two variables out of said group of variables, and incorporating said two measured variables into the plurality of discriminant functions.

8. A method according to claim 6, comprising measuring three variables out of said group of variables, and incorporating said three measured variables into the plurality of discriminant functions.

9. A method according to claim 6, comprising measuring four variables out of said group of variables, and incorporating said four measured variables into the plurality of discriminant functions.

10. A method according to claim 6, comprising measuring all the variables of said group of variables, and incorporating said measured variables into the plurality of discriminant functions.

* * * * *

UNITED STATES PATENT AND TRADEMARK OFFICE
CERTIFICATE OF CORRECTION

PATENT NO. : 4,417,478
DATED : November 29, 1983
INVENTOR(S) : M. C. Jon, V. Palazzo, G. W. Sturm It is certified that error appears in the above—identified patent and that said Letters Patent is hereby corrected as shown below:

On the title page, in the Abstract, column 2, line 11 "threshold, to" should read --threshold, and--.

In the specification, Column 1, line 43 "manner" should read --number--. Column 1, line 59 "determined" should read --determining--. Column 2, line 47 "FIGS. 5a to 5c" should read --FIG. 5--. Column 5, line 59 "$|b_i|$" should read --$|\vec{b}_i|$--. Column 7, line 12 "for determining" should read --of determining--.

Signed and Sealed this

Twenty-seventh Day of March 1984

[SEAL]

Attest:

GERALD J. MOSSINGHOFF

Attesting Officer

Commissioner of Patents and Trademarks